United States Patent
Letort et al.

(10) Patent No.: US 7,060,038 B2
(45) Date of Patent: Jun. 13, 2006

(54) DEVICE FOR DELIVERING A SENSOR TO THE ENDOVASCULAR SYSTEM AND METHOD OF USE

(75) Inventors: Michel Letort, Prevessins (FR); Brian Raze, Windsor, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 427 days.

(21) Appl. No.: 10/422,639

(22) Filed: Apr. 24, 2003

(65) Prior Publication Data

US 2004/0215070 A1    Oct. 28, 2004

(51) Int. Cl.
*A61B 5/00*    (2006.01)

(52) U.S. Cl. .................. 600/549; 600/561; 600/505; 600/485; 600/481

(58) Field of Classification Search ........... 600/549, 600/300, 345, 347, 365, 486, 505, 561; 623/1.11; 606/195
See application file for complete search history.

(56) References Cited

U.S. PATENT DOCUMENTS

| | | | |
|---|---|---|---|
| 4,846,191 A | 7/1989 | Brockway et al. | |
| 5,772,669 A * | 6/1998 | Vrba | 623/1.11 |
| 6,159,156 A | 12/2000 | Van Bockel | |
| 6,416,474 B1 | 7/2002 | Penner et al. | |
| 6,442,413 B1 * | 8/2002 | Silver | 600/345 |
| 6,447,522 B1 | 9/2002 | Gambale et al. | |
| 6,447,540 B1 | 9/2002 | Fontaine et al. | |
| 6,497,681 B1 | 12/2002 | Brenner | |
| 6,517,569 B1 | 2/2003 | Mikus et al. | |
| 6,533,806 B1 * | 3/2003 | Sullivan et al. | 623/1.11 |
| 6,699,186 B1 * | 3/2004 | Wolinsky et al. | 600/300 |

* cited by examiner

*Primary Examiner*—Max F. Hindenburg
*Assistant Examiner*—Brian Szmal
(74) *Attorney, Agent, or Firm*—Janis J. Biksa (57) ABSTRACT

A delivery system for delivering a sensor to a body cavity includes a catheter and sheath slidably or rotatably coupled to the catheter. The sheath may be retractable and peelable. The delivery device may include an expandable balloon or a crushable material capable of moving the sensor laterally away from the catheter, to the target site. One embodiment of the delivery system includes a deployment device comprising a cord operably engaged with a pulley, and attached at the distal end to a cap engaged with the sensor. Another embodiment of the delivery system comprises a catheter having a chamber that can accommodate the sensor, and a sheath slidably coupled to the exterior of the catheter, and covering the chamber when the sheath is in the closed position. Further included is a method of delivering a sensor to a body cavity using any of the embodiments of the delivery system.

38 Claims, 8 Drawing Sheets

DEVICE FOR DELIVERING A SENSOR TO THE ENDOVASCULAR SYSTEM AND METHOD OF USE

TECHNICAL FIELD OF THE INVENTION

The present invention relates generally to a device for the introduction of a sensor into a human or animal body, especially into a blood vessel.

BACKGROUND OF THE INVENTION

Vascular aneurysms are produced when a thinning or weak spot in a vessel wall dilates, eventually posing a health risk from its potential to rupture, dissect, cause blood clots, or internal bleeding. While aneurysms can occur in any blood vessel, most occur in the aorta and peripheral arteries. The majority of aortic aneurysms occur in the abdominal aorta, usually beginning below the renal arteries and often extending into one or both of the iliac arteries. The etiology of aneurysm formation is not entirely understood, but is thought to be related to congenital thinning of the artery, atherosclerotic vessel degeneration, vessel trauma, infection, smoking, high blood pressure, and other causes leading to vessel degeneration. Left untreated, aneurysms may lead to gradual vessel expansion, thrombus formation leading to stroke or other vessel blockage, vessel rupture, shock, and eventual death.

Aneurysms may be treated in open surgical procedures, where the diseased vessel segment is bypassed and repaired with an artificial vascular graft. However, the surgical procedure is complex and requires experienced surgeons and well equipped surgical facilities. Patients suffering from such aneurysms are often elderly and weakened from cardiovascular and other diseases. This factor reduces the number of patients eligible for surgery. Furthermore, conventional aneurysm repair has a relatively high mortality rate, usually from 2 to 10%. Morbidity related to the surgery includes myocardial infarction, renal failure, impotence, paralysis, and other conditions. Even with successful surgery, recovery takes several weeks and often requires a lengthy hospital stay.

To overcome some of the drawbacks associated with open surgery, a variety of endovascular prosthesis placement techniques have been developed. Without the need for open surgery, patient complications and recovery time may be significantly reduced. One endovascular aneurism repair technique involves a tubular prosthesis deployed by remote insertion through a femoral artery. A stent-graft prosthesis permits a sealed shunt of blood flow from a healthy portion of the aorta, through the aneurysm, and into one or both of the iliac artery branches. The prosthesis excludes any thrombus present in the aneurysm while providing mechanical reinforcement of the weakened vessel reducing the risk of dissection and rupture. Furthermore, the prosthesis can substantially reduce the blood pressure within the isolated aneurysmal sac providing the weakened vessel with a favorable healing environment. Backflow from blood vessels in communication with the aneurismal sac may continue to pressurize the aneurysm despite the presence of a shunt.

A known shortcoming of some of the implantable endovascular prosthetics relates to migration and seal. The affected vessel(s) may vary widely in location, size, and the distended shape of the aneurysm itself. Particularly after treatment, the aneurysm and associated vessels may drastically change morphology thereby exerting stress forces on the deployed prosthesis. With sufficient change in aneurysm morphology and subsequent stress placed on the prosthesis, the device may migrate and/or detach from the vessel wall. As a result, the fluid seal may be compromised and blood may leak into the aneurysm from the aorta thereby elevating the aneurysmal pressure. The patient may have to undergo another treatment to prevent undetected "endoleakage" leading to aneurysm growth or regrowth, or other more serious problems associated with aneurysms. Accordingly, it would be desirable to provide a strategy for monitoring an aneurysm.

Current strategies for monitoring aneurysms involve imaging by means of CT-scan, magnetic resonance, angiography, duplex ultrasound, and the like. These imaging methods may utilize a contrast solution to enhance the visualization process. Some patients may be allergic to the iodine based contrast solutions and other "dyes". In rare situations, the patient may suffer from anaphylactic responses involving mental confusion, dizziness (due to a drop in blood pressure), swelling (especially of the face, tongue and throat), and difficulty breathing. The reactions can be serious if not treated immediately. Therefore, it would be desirable to provide a strategy for monitoring an aneurysm without the use of appreciable volumes of contrast solution.

Another shortcoming of the aforementioned imaging strategies relates to sensitivity. Current methods may effectively visualize the size and shape of the aneurysm, providing a passive monitoring strategy. However, such methods may not effectively detect the presence of an endoleak. For example, if the aneurysm is largely filled with a thrombus, a sufficient amount of contrast solution may not be introduced into the aneurysm. This circumstance may lead to a reduced capacity to detect endoleakage. Continued undetected endoleakage, even at a low level, may slow or even reverse the aneurysmal healing process. To avoid this and other situations where endoleakage cannot be detected, it may be advantageous to measure endoleaks directly. Therefore, it is desirable to provide a sensing device and method for determining aneurismal pressure that overcomes the aforementioned and other disadvantages.

One such pressure-sensing device is disclosed in U.S. Pat. No. 4,846,191. Use of this device entails placing the tip of a pressure-transmitting catheter within a blood vessel or other structure within which pressure is to be measured. The catheter transmits the pressure signal to a transducer, which is typically connected to amplifying electronics and an implantable radio-transmitter capable of relaying the pressure information to a radio receiver located outside the body. Although such a device is capable of delivering pressure measurements from within the vasculature, it requires a complex device including a sizable implant in a body cavity.

Recently, miniaturized pressure sensors have been developed that can be placed directly into an aneurismal sac, and transmit pressure data to a receiving device outside the body. One such pressure sensor is disclosed in U.S. Pat. No. 6,159,156. This pressure sensor may be used in conjunction with an endoprosthesis and may be delivered with a catheter. U.S. Pat. No. 6,416,474 describes a sensor attached to a loop. The loop may encircle a tubular prosthesis, and may facilitate delivery of the sensor. The development of miniaturized sensors and other devices intended for use in the vascular system has created a need for a means of delivering them.

Various catheter-based systems have been developed to deliver medical devices and drugs to target sites within the body. U.S. Pat. No. 6,159,156 discloses use of a standard or specialized catheter for deploying a pressure sensor. The sensor is deployed by pushing it from the distal tip of the catheter, a process that may damage the sensor. U.S. Pat. No. 6,416,474 discloses a delivery system for a sensor attached to a loop. The delivery system includes a flexible catheter with a means of attaching the sensor via the loop to the distal end of the catheter, and an actuator for releasing the sensor that may be activated from the proximal end of the catheter. This delivery system is useful only for sensors or other medical devices that include a loop.

U.S. Pat. No. 6,447,522 discloses a delivery system for delivering tubular implants through the vascular system and placing them within tissue. One embodiment according to the invention includes a shaft with an outer tube that compresses and "crinkles" to a larger diameter in order to engage the inside surface of the implant. The outer tube can be extended to release the implant. Alternatively, the implants may be retained on the shaft by oval-shaped cross sections. A slidable cam within the shaft engages the oval areas, deforming them to a circular shape and releasing the implants. According to another embodiment, the implant is placed over a plunger that is driven by a pressurized fluid. This delivery system is clearly designed to deliver tubular or ring-shaped implants, and would not be useful for solid implants.

Recently, catheter-based delivery systems have been disclosed that include a sheath composed of a soft, pliable material, such as polyamide, polyurethane, polyimide, polytetrafluroethylene (PTFE), fluorinated ethylene propylene, or other medically acceptable polymers. To facilitate retraction, the sheath may be designed to be easily split along a longitudinal axis, and is referred to as a peelable sheath. Sheaths fulfill a variety of functions in catheter-based delivery systems such as allowing flexibility of the body of the delivery system, protecting the device being delivered, facilitating placement and retraction of the delivery device, and minimizing the potential for tissue injury. For example, U.S. Pat. No. 6,497,681 discloses a method for delivering a cardiac pacing lead or other elongated flexible device using a peelable introducer sheath and a device to cut or split the sheath longitudinally as it is retracted proximally and withdrawn from the body. In this instance, the peelable sheath facilitates retraction of the delivery device. U.S. Pat. No. 6,517,569 discloses a prostatic stent delivery device with a peel-away sheath that controls stent expansion during deployment, and can then be easily retracted. U.S. Pat. No. 6,533,806 discloses a delivery system including a balloon catheter and a sheath that surrounds and maintains an expandable prosthesis in a compressed condition until it arrives at the delivery site.

The above examples disclose highly specialized delivery systems that are not widely applicable for purposes other than those for which they were designed. Therefore, it would be desirable to provide a means of delivering a solid, spherical or oblong pressure sensor into the vascular system, especially into an aneurismal sac.

SUMMARY OF THE INVENTION

One aspect according to the invention provides a delivery system for a sensor and lead that includes a catheter with an attached sheath that surrounds the sensor and lead. The sheath is retractable and/or peelable, and slidably attached to the catheter. One embodiment of the delivery system includes a deployment device that causes the sensor to be disengaged from the delivery system at the target site. The deployment device includes a cap that is engaged with the distal end of the sensor, and a cord attached to the distal side of the cap. Further, the cord is operably engaged with a pulley, so that the cap separates from the sensor when the distal end of the cord is pulled.

Another aspect according to the invention provides a delivery system for a sensor with a lead operable attached to the sensor that includes a catheter and a sheath rotatably coupled to the catheter. The sheath has a delivery opening formed in a delivery side of the sheath. According to this embodiment, the delivery system further includes a biasing member positioned within the sheath that causes the sensor to move through the delivery opening and be delivered to the target site when the sheath is rotated so that the delivery opening is aligned with the sensor.

Another aspect according to the invention provides a delivery system for a sensor with a lead that comprises a catheter with a peelable sheath, and a biasing member, in which both the sheath and biasing member are attached to the catheter. The sheath is perforated along its entire length. The biasing member comprises an expandable balloon positioned within the sheath, the balloon being connected by a lumen to a reservoir of liquid or flowable gel at the proximal end of the device. Filling the balloon with the liquid or flowable gel from the reservoir causes it to expand and to press against the perforated, peelable sheath, to form a break line along the length of the sheath, and to push the sensor and lead through the opening thus formed.

Another aspect according to the invention provides a delivery system for a sensor and lead, comprising a catheter having a chamber proximate the distal end of the catheter, and a sheath slidably coupled to the exterior surface of the catheter and covering the chamber when the sheath is in the closed position. Further, a wire connected to the proximal end of the sheath is pushed toward the distal end of the catheter in order to cause the sheath to slide toward the distal end of the catheter to an open position. From the open position, the wire may be pulled to cause the sheath to return to its closed position.

Another aspect according to the invention provides a method for delivering a sensor, with or without a lead within a body cavity such as a blood vessel or aneurismal sac. The method includes using any of the above delivery systems, and advancing the catheter along a pre-positioned guide wire until the distal portion of the catheter reaches the target site. The method further includes deploying a sensor, with or without a lead, from the catheter to the target site. The sensor may be deployed in conjunction with the placement of an endoluminal prosthesis to treat an aneurism.

DETAILED DESCRIPTION

Figure 1A:
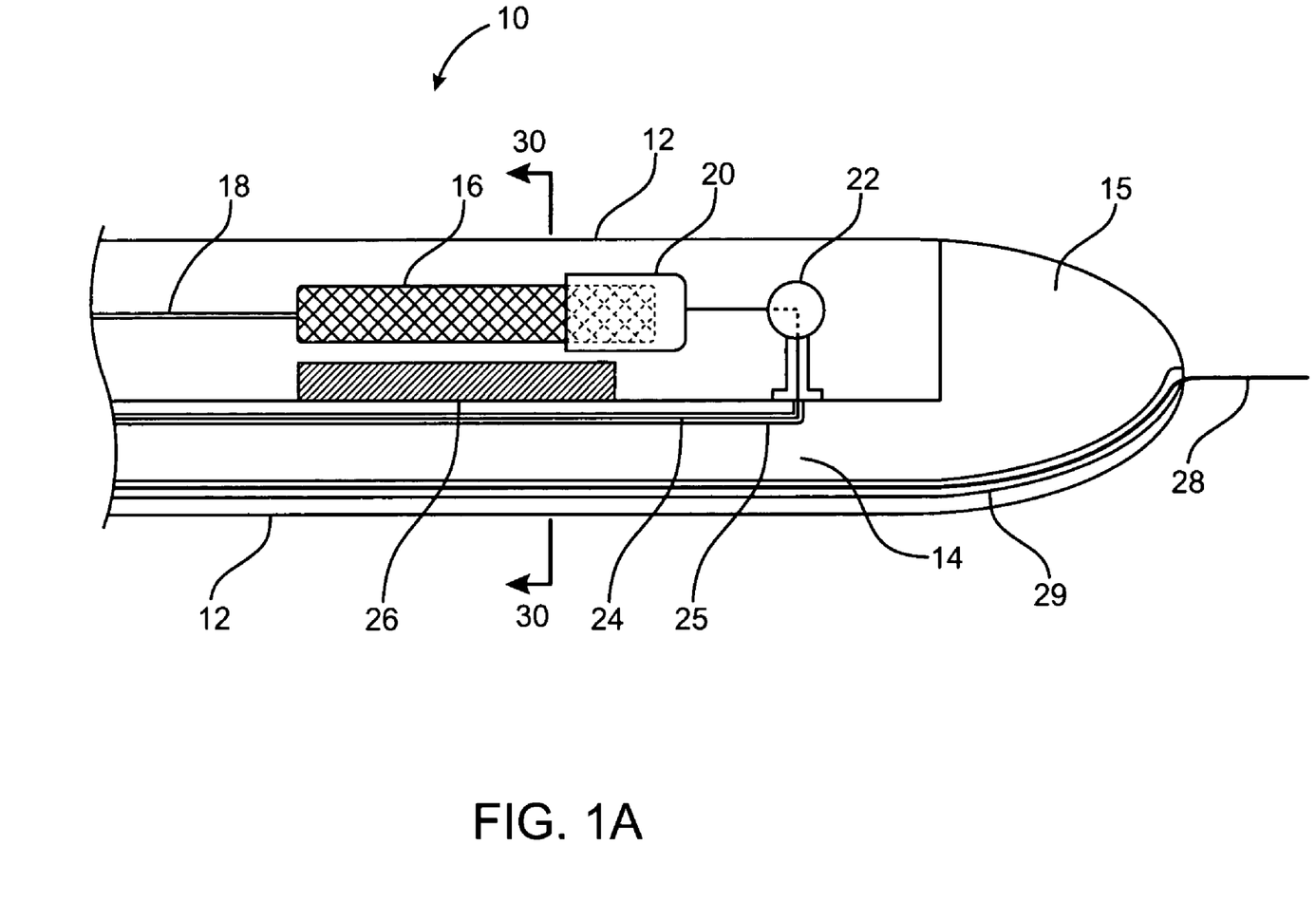
FIG. 1A is a cross-sectional side view of a device for delivering a sensor and lead, in accordance with the present invention.

Referring to the drawings, FIG. 1A is cross-sectional side view of a device 10 for delivering a sensor and lead according to the present invention. The sensor 16 may be any of various implantable medical devices used to monitor conditions such as pressure, temperature, oxygen saturation, or other parameters at a target site within the body. In some embodiments, the sensor has a lead 18 attached to it for the purpose of transmitting data to a recorder. Alternatively, the data may be transmitted using imaging techniques, and no lead is required. A sensor, with or without a lead attached to it, may be used in any body cavity, such as a cardiac chamber, the vascular system, an aneurismal sac within the vascular system, the pleural cavity, the spinal column, an ocular chamber, a cochlea, a subarachnoid space, a cerebral space and any other pressurized body cavity. In medical practice, a pressure sensor is frequently used to monitor pressure at a specific site within the vascular system, for example, within an aneurismal sac.

Device 10 includes a catheter body 14 having a tapered or rounded nose cone 15. The catheter body 14 is typically made of a flexible, biocompatible polymeric material such as polyurethane, polyethylene, PEBAX, PVC, nylon, and polytetrafluroethylene (PTFE). In some embodiments, the catheter 14 has a lumen 29 that can accommodate a guide wire 28. The lumen 29 runs longitudinally through the catheter 14, so that the catheter may be slipped over the guidewire, and, when no longer needed, the guide wire may be withdrawn through the lumen of the catheter. A guidewire 28 is typically of metallic construction, and is inserted through the femoral artery and threaded through the vascular system to the target site. The catheter is slipped over the guidewire, and guided along the vascular route, until both the guidewire and catheter are at their desired target locations.

Attached to catheter 14 at the proximal end of the nose cone 15, is a sheath 12 that covers the distal portion of the catheter including the sensor 16 and lead 18, and presents a smooth outer surface. In addition, sheath 12 maintains the sensor 16 and the lead 18 attached to the sensor in close proximity to the catheter 14 until the catheter is placed at a target site within a blood vessel, such as an aneurismal sac. Sheath 12 is perforated at the site where it is attached to the nose cone 15, and is retractable. A cap 20 covers, and is engaged with, the distal end of sensor 16. The cap 20 is made of a biocompatible polymeric material such as polyurethane, polyethylene, nylon, and polytetrafluroethylene (PTFE), or metals and metallic alloys, such as titanium and steel. Cap 20 is loosely fitted over the distal end of the sensor 16. The cap 20 holds the sensor 16 in place, adjacent the catheter 14, but readily disengages from the sensor 16 when pulled longitudinally away from the sensor 16. Attached to the exterior surface of cap 20 is a cord 24. Cord 24 is operably engaged with pulley 22, and extends through a lumen 25 running longitudinally through the catheter 14 to the proximal end of the delivery device. Attached to the catheter 14, and adjacent to the sensor 16 is biasing member 26. In one embodiment according to the invention, biasing member 26 comprises of a sponge-like material such as an open cell sponge, a polyurethane foam, hydro-gel based materials, a self-expanding polymer or self-expanding polymer mix, a metal spring comprising, for example, nitinol, or any other biocompatible, readily compressible material. The biasing member 26 is maintained in its' compressed state, pressing against the sensor 16 until the cap 20 is removed from the sensor 16. As soon as the sheath is retracted and the cap is removed from the sensor, the biasing member expands to an expanded state. Further, biasing member 26 is of sufficient size so that as it reaches its' fully expanded state, it moves the sensor 16 away from the catheter 14 and into the target site. In another embodiment, biasing member 26 comprises an expandable balloon, that is connected to a lumen (not shown), the lumen being flowably connected to a reservoir of flowable gel or liquid at the proximal end of the device. The reservoir may be a compressible chamber or bladder, or a syringe with a plunger, or any other configuration that enables the operator to easily move the flowable gel or liquid from the reservoir to the balloon. To deploy the sensor, the flowable gel or liquid is forced from the reservoir into the balloon, causing it to expand and move the sensor laterally to the target site.

To deliver the sensor, a guide wire 28 is positioned within the blood vessel. The catheter 14 is then be advanced along the guide wire 28, through the blood vessel until distal portion of the catheter 14 is positioned within an aneurismal sac or other target site. The position of catheter 14 may be determined by visualization methods known in the art, such as fluoroscopy or ultrasound.

After appropriate catheter 14 positioning, the sensing device is deployed. The sheath 12 is at least partially retracted toward the proximal end of the delivery device by pulling on the proximal end of the sheath 12, and causing it to detach from the nose cone 15 of catheter 14. The sheath 12 is retracted sufficiently to expose the sensor 16. Next, the cord 24 is pulled from the proximal end, so that the cap 20 is pulled from the end of the sensor 16, freeing it from the catheter 14. When the cap 20 is disengaged from the sensor, the biasing member 26 expands causing the sensor 16 to move laterally away from the catheter 14, into the target site. The sheath 12 is then fully retracted, releasing lead 18. Finally, the catheter is retracted from the target site.

Figure 1B:
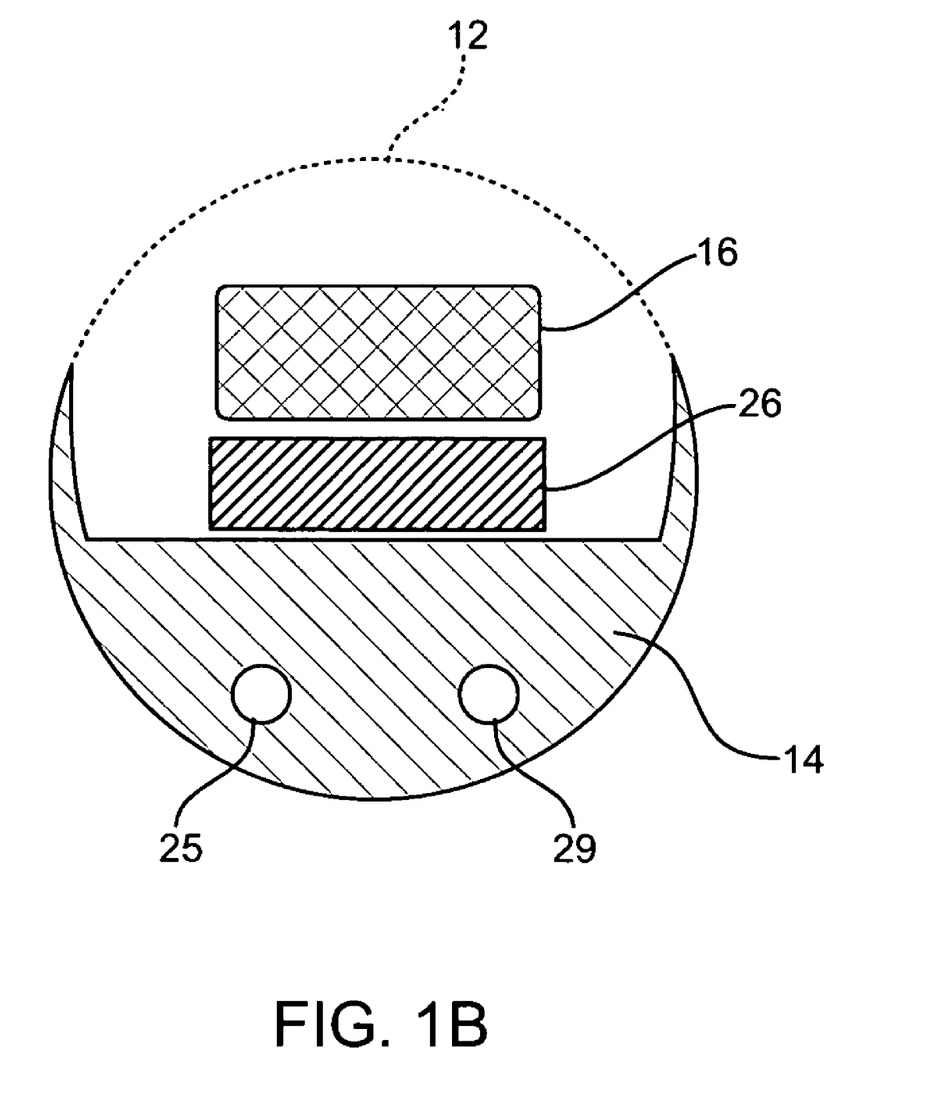
FIG. 1B is a cross-sectional end view of the device shown in FIG. 1A, taken at 30—30.

FIG. 1B provides a cross sectional view of the delivery device 10, taken at 30—30 in FIG. 1A. Catheter body 14 includes lumen 25 to accommodate the cord 24, and lumen 29 for the guide wire 28. The peelable and retractable sheath 12 is attached to the catheter body 14. Deployment device 26 may be either a crushable material or an expandable balloon, capable of moving sensor 16 away from the catheter and to the target site.

Figure 2:
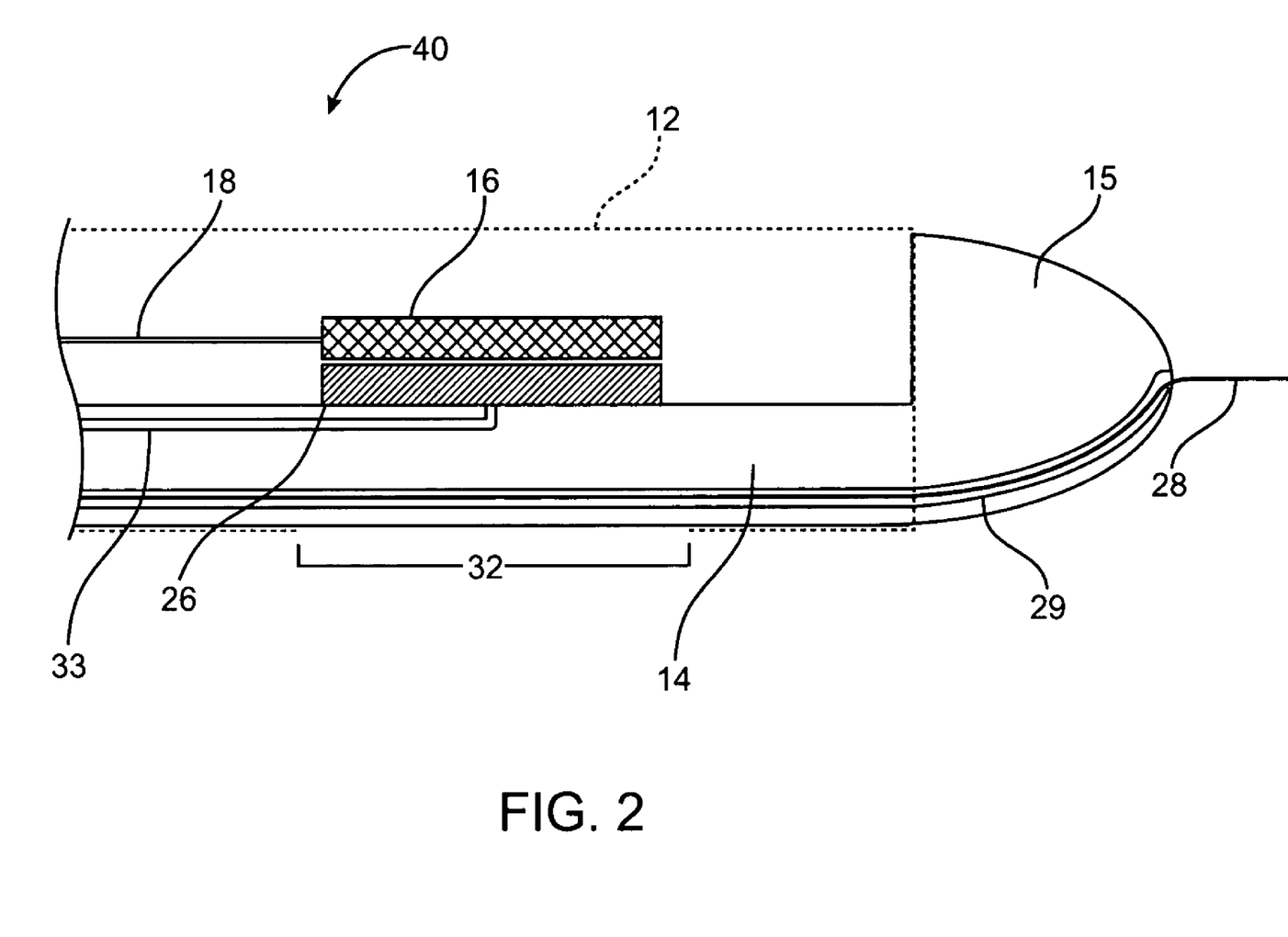
FIG. 2 is a cross-sectional side view of a second device for delivering a sensor and lead in accordance with the present invention.

FIG. 2 provides a cross sectional side view of the delivery device 40, a second embodiment of the invention. This delivery device includes a catheter body 14 with a tapered nose cone 15, and optionally, a lumen 29 to accommodate guide wire 28. A sheath 12 is rotatably attached to the proximal end of the catheter nose cone, and covers the sensor 16 and lead 18. The lead 18 may not be present, if not required for the functioning of the sensor 16. Deployment device 26 may be either a compressible material or an expandable balloon. If deployment device 26 consists of an expandable balloon, it is connected to a lumen 33, the lumen being connected to a reservoir of flowable gel or liquid at the proximal end of the device, as is known in the prior art. If a compressible material is used, it is maintained in its compressed state by the sensor 16 and sheath 12 until the sheath 12 is opened. The sheath 12 includes an oblong opening 32, large enough for the sensor 16 to pass through. As shown in FIG. 2, the sheath 12 is in the closed position, with the opening 32 oriented away from the sensor 16. To facilitate retraction of the sheath 12, the proximal portion of the sheath 12 may be perforated longitudinally, so that it is peelable.

Figure 3A:
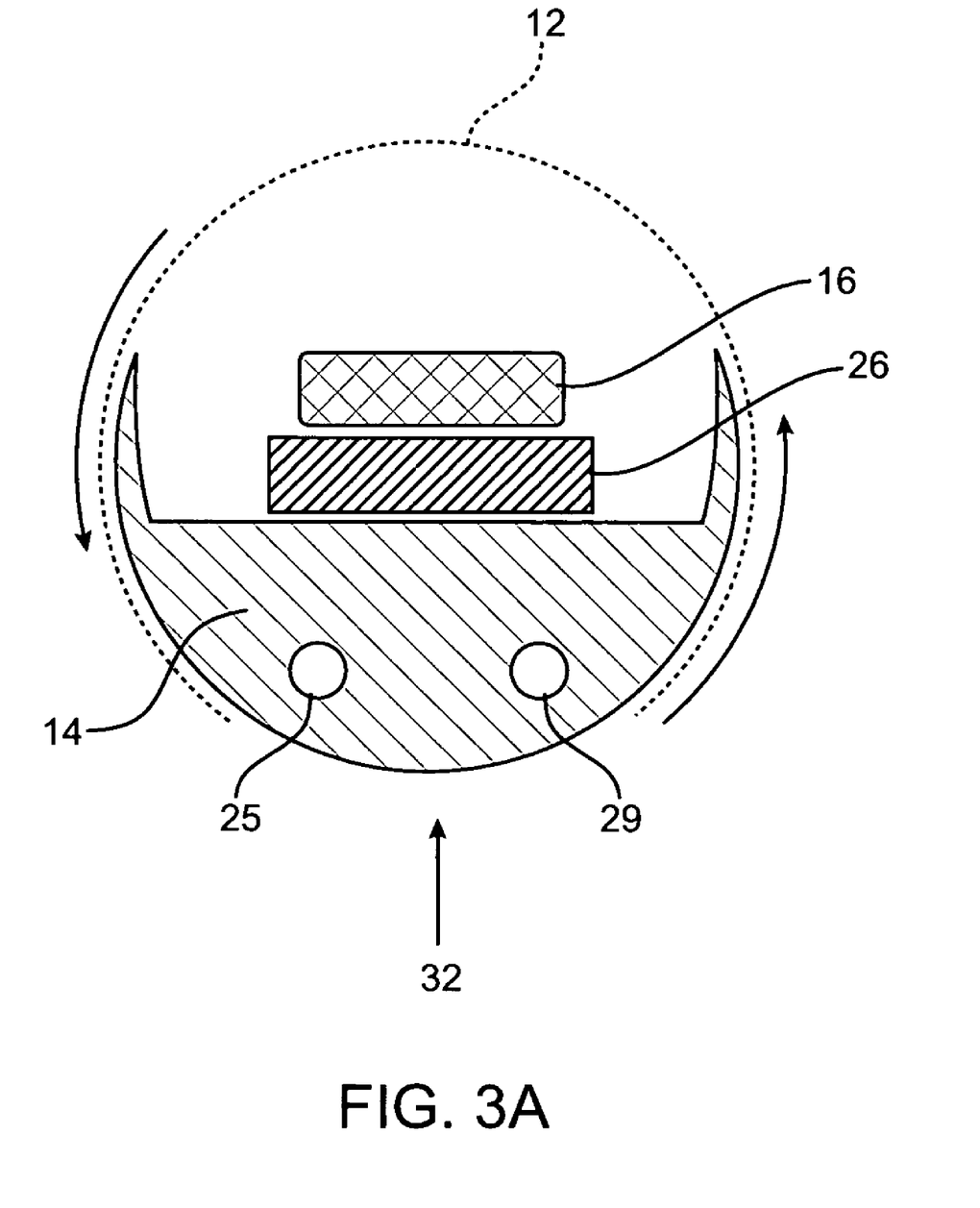
FIG. 3A is a cross-sectional end view of the device of FIG. 2 with the rotatable sheath in the closed position.
Figure 3B:
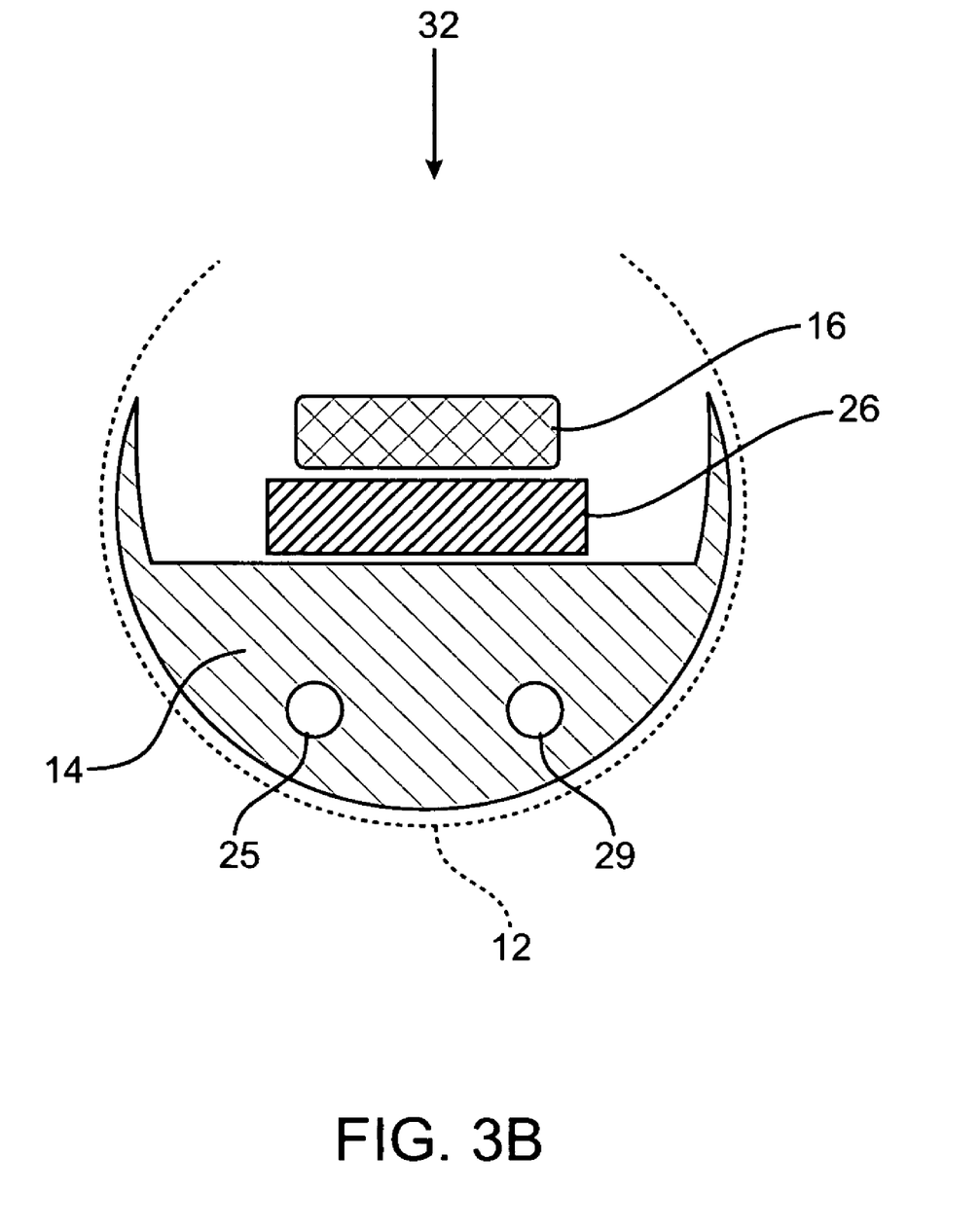
FIG. 3B is a cross-sectional end view of the device of FIG. 2 with the rotatable sheath in the open position.
Figure 3C:
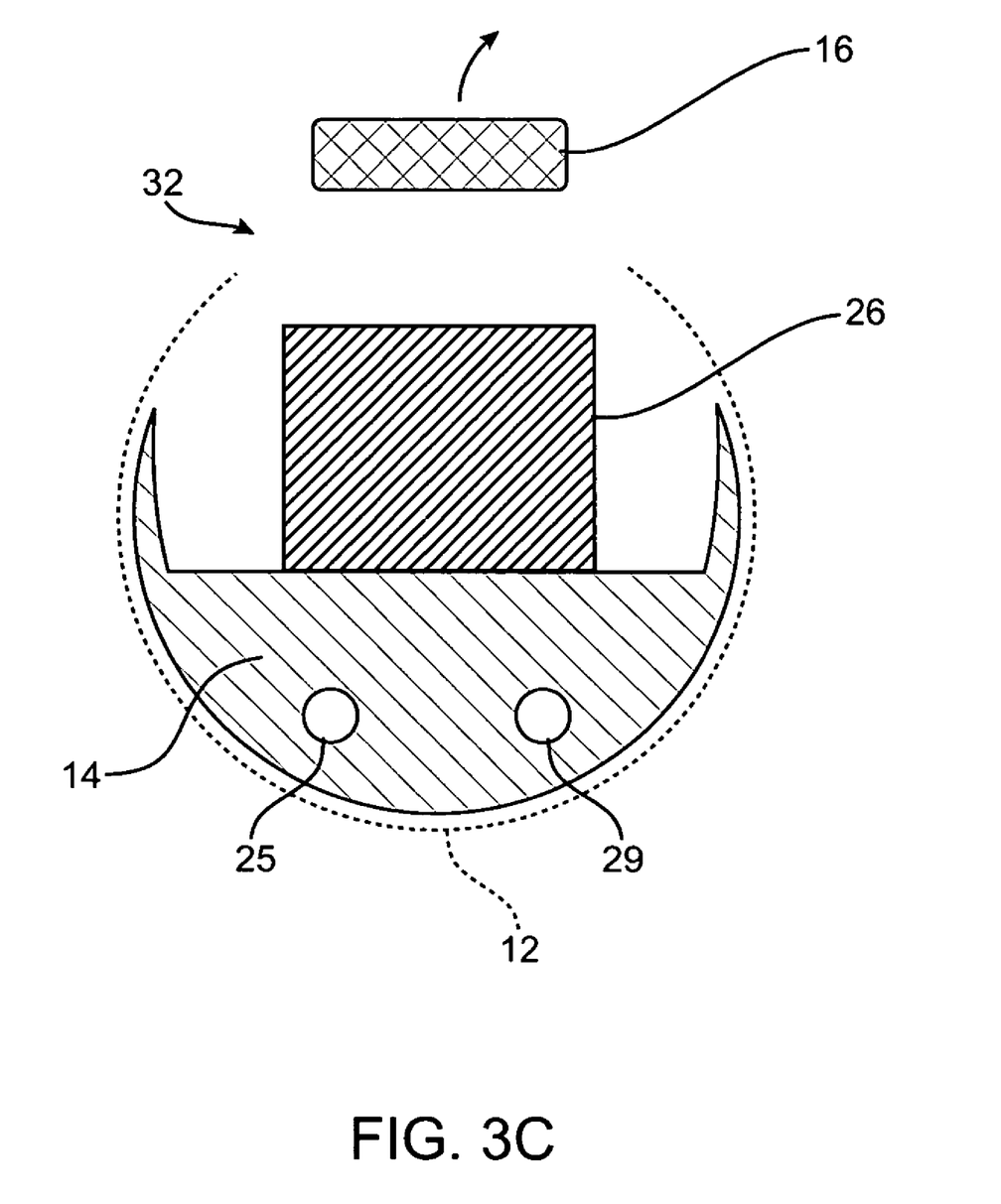
FIG. 3C is a cross-sectional end view of the device of FIG. 2 with the rotatable sheath in the open position and the biasing member in its' expanded form, causing the sensor to move laterally, away from the catheter toward the target site.

To deliver the sensor 16, the distal portion of the catheter 14 is positioned within an aneurismal sac or other target site by following pre-positioned guide wire 28, as is known in the prior art. The sheath 12 is in the closed position during placement of the catheter 14, having the opening 32 through the sheath 12 oriented away from the sensor 16. Next, the sheath 12 is rotated about the longitudinal axis of the catheter 14 as shown in FIG. 3A, so that the opening through the sheath 32 is adjacent the sensor 16, as seen in FIG. 3B. Deployment device 26 expands when the sheath 12 is in the open position, causing the sensor 16 to move laterally away from the catheter 14, into the target site. The sensor may be imaged to assure accurate placement at the target site. The sheath 12 is then retracted by grasping the proximal end, and separating the two longitudinal halves of the sheath along the longitudinal perforations. The catheter portion of the delivery device is then retracted and removed from the body.

Figure 4A:
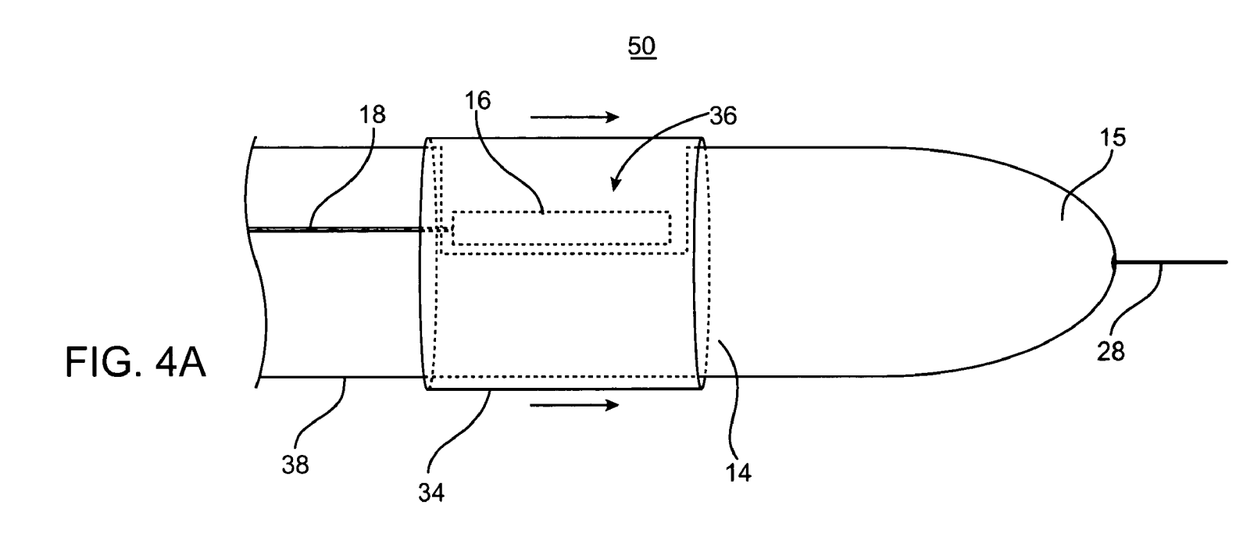
FIG. 4A is a cross-sectional side view of a third device for delivering a sensor, with or without a lead, in accordance with the present invention. The slidable sheath of this embodiment is in the closed position.
Figure 4B:
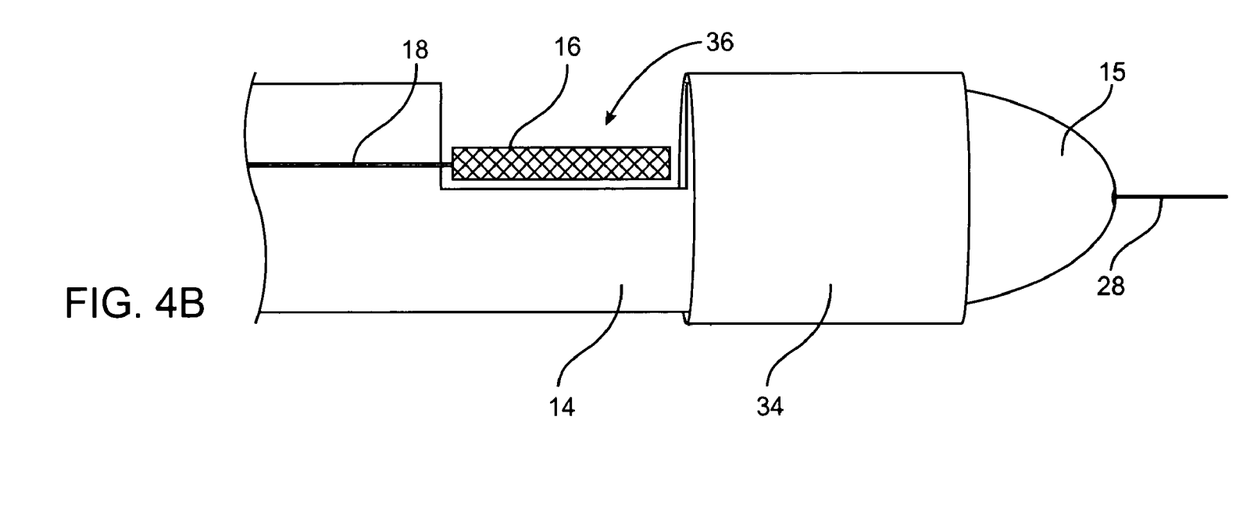
FIG. 4B is a side view of a third device for delivering a sensor with or without a lead, in accordance with the present invention. The slidable sheath of this embodiment is in the open position.

A third embodiment of the present invention is shown in FIG. 4A and FIG. 4B. Delivery device 50 includes a catheter 14 with a tapered or rounded nose cone 15. Proximal to the nose cone 15, is a chamber 36 of a size that can accommodate the sensor 16. The lead 18, if present, is disposed along the exterior of the catheter 14, held in place by any appropriate bioadhesive, for example, a glucose-based bioadhesive, or with a hook at the proximal part of the sensor. Slidably attached to the catheter 14 is a sheath 34, placed so that it covers the chamber 36 when in the closed position (FIG. 4A), and presents a smooth exterior. Attached to the proximal end of the sheath 34 is a wire or lever 38 that provides a means of moving the sheath 34. When the sheath 34 is in the closed position, as in FIG. 4A, the wire or lever 38 may be pushed to move the sheath 34 forward along the catheter toward the nose cone 15, until it is in the open position (FIG. 4B). From the open position, the sheath 34 may be returned to the closed position by pulling on the wire or lever 38.

To deliver the sensor 16, the distal portion of the catheter 14 is positioned within an aneurismal sac or other target site by following pre-positioned guide wire 28. To release the sensor 16, the sheath 34 is slid toward the catheter 14 tip, to the open position, as shown in FIG. 4B. Once the sensor is released, the sheath 34 is repositioned over the chamber 36 by pulling on the wire or lever 38. This will present a smooth surface, and minimize the potential for tissue damage during manipulation and retraction of the catheter 14. The catheter 14 is then retracted and removed from the body.

Figure 5:
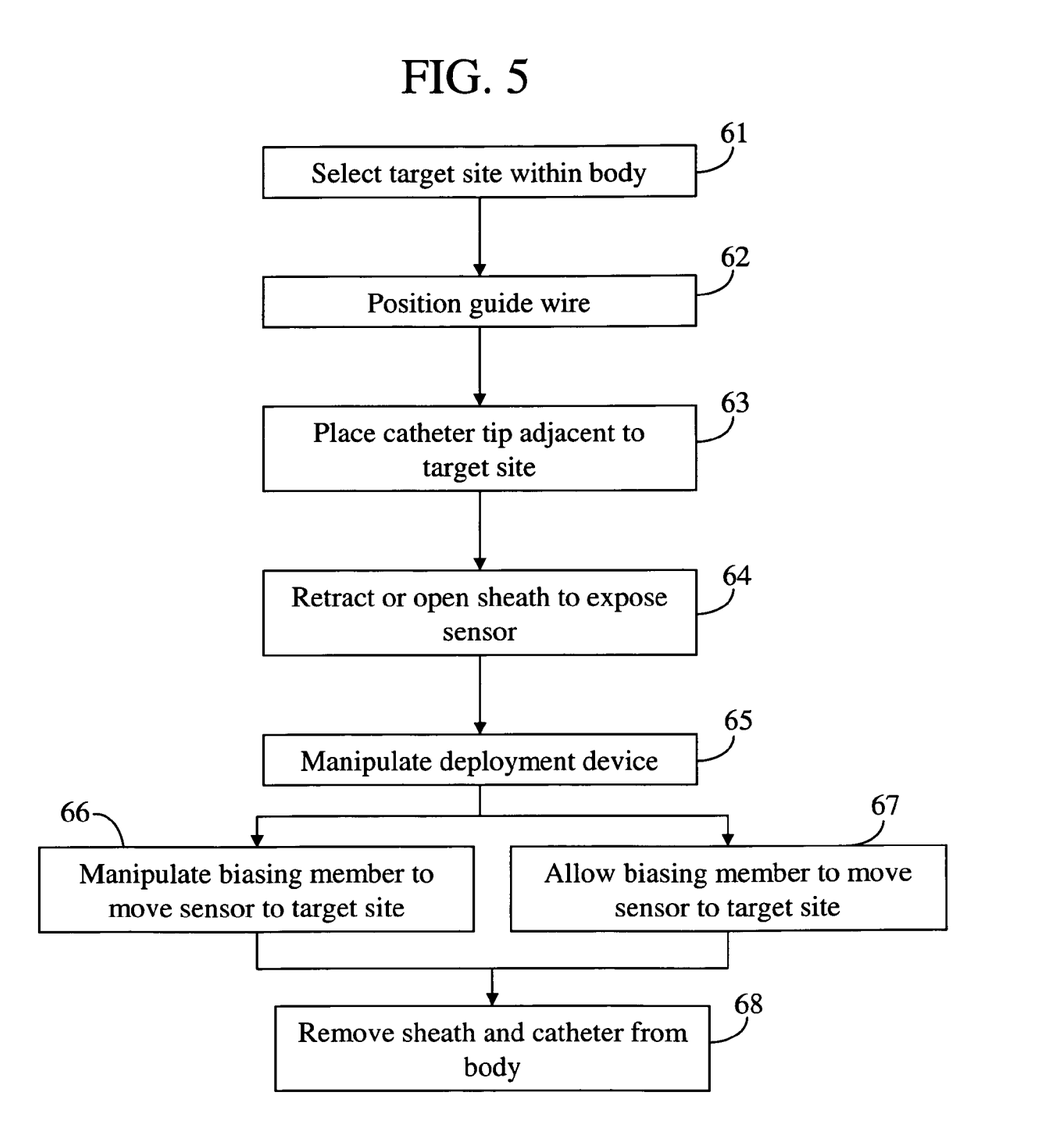
FIG. 5 is a flow diagram of a method of placing a sensor within a body cavity using a delivery device in accordance with the present invention.

FIG. 5 shows a flowchart of an embodiment of the invention comprising a method 60 for placing a sensor at a target site within a body cavity. The method begins at block 61 wherein a target site is selected where a sensor will be placed. In this example the target site selected is an aneurismal sac within the vascular system. A guide wire is generally used to guide a catheter through the vascular system (block 61). The guide wire is inserted into the vascular system, typically through an incision in the femoral artery, and passed through the vascular system to the targeted aneurismal sac, as indicated in block 62. The catheter carrying the sensor is then slipped over the guide wire and guided through the vascular system until the distal tip of the catheter is at its' desired target location within the aneurismal sac where the sensor is to be deployed (block 63). At block 64, the sheath attached to the catheter is opened or retracted so that the sensor is exposed to the interior of the aneurismal sac, and there is a clear path to the target site where the sensor is to be placed. The manipulations required will depend on the configuration of the delivery catheter and sheath. For example, if the device in FIG. 1 is used, the sheath is retracted sufficiently to expose the catheter. For the catheter configuration in one embodiment according to the invention, the sheath is rotated so that the delivery opening is adjacent the sensor. In another embodiment, the sheath is slid toward the distal tip of the catheter. In yet another embodiment of the invention, the sheath is split along a longitudinal perforated line. At block 65, the sensor is released from the catheter if necessary, depending on the configuration of the delivery device. For example, if the device shown in FIG. 1 is used, the cap is disengaged from the distal end of the sensor by pulling the cord operably engaged with the pulley. At blocks 66 and 67, a biasing member is used to move the sensor from the catheter to the target site. Depending on the configuration of the delivery device, the biasing member is either a compressible material or an expandable balloon. If a compressible material is used, it is allowed to expand. If an expandable balloon is used, a flowable gel or liquid is forced from a reservoir at the proximal end of the device into the balloon causing it to expand. In either case, the biasing member pushes the sensor away from the catheter to the target site. As indicated at block 68, the sheath and catheter are then removed from the body. Depending on the configuration of the device, the sheath may be retracted by peeling it along a longitudinal axis and removing it from the body separately from the catheter. Alternatively, the sheath may be placed in a closed position by either sliding or rotating it so that the chamber that held the sensor is covered, and the catheter has a smooth exterior. Then the catheter and sheath are retracted and removed from the body.

While the embodiments according to the present invention are disclosed herein, various changes and modifications can be made without departing from the spirit and scope of the invention. For example the delivery system may be used with a variety of sensors and in conjunction with an array of endoluminal prostheses, and the order of the deployment steps may be varied without limiting the utility of the invention.

What is claimed is:

1. A delivery system for delivering a sensor into a target site comprising:
   a catheter;
   a perforated sheath coupled to the catheter;
   a sensor within the sheath;
   a deployment device positioned within the sheath, the deployment device including a cord operably engaged with a pulley and attached at a distal end to a cap, the cap engaged with the sensor, wherein, when the system is delivered into the target site, the sheath is at least partially peeled, and a proximal end of the cord is pulled to separate the cap from the sensor.

2. The system of claim 1 further comprising a biasing member contacting the sensor, wherein the biasing member moves the sensor laterally when the cap is separated from the sensor.

3. The system of claim 1 wherein the sensor is selected from a group consisting of a pressure sensor, a temperature sensor, an oxygen sensor and a flow rate sensor.

4. The delivery system of claim 1 wherein a lead is operably attached to the sensor.

5. The system of claim 1 wherein the target site is a body cavity selected from the group consisting of a blood vessel, an aneurismal sac within a blood vessel, a cardiac chamber, a pleural cavity, a spinal column, an ocular chamber, a cochlea, a subarachnoid space, and a cerebral space.

6. The system of claim 2 wherein the biasing member is comprised of a compressible material such that when the sheath is at least partially peeled, the biasing member expands in a direction lateral to the length of the catheter and pushes the sensor to the target area.

7. The delivery system of claim 2 wherein the biasing member is comprised of an expandable balloon and a lumen flowably connected to the balloon and to a reservoir of liquid or flowable gel at the proximal end of the catheter, wherein when the system is delivered to the target site, the balloon is expanded by filling it with the liquid or flowable gel from the reservoir, causing the balloon to expand and push the sensor laterally to the delivery site.

8. A delivery system for delivering a sensor to a target site comprising:
   a catheter;
   a sheath rotatably coupled to the catheter, the sheath including a delivery opening formed in a delivery side of the sheath;
   a sensor positioned within the sheath and spaced apart from the delivery side of the sheath;
   a deployment means wherein, when the system is delivered into the target site, the sheath is rotated until the delivery opening is aligned with the sensor to allow the sensor to be delivered via a biasing member into the target site through the delivery opening.

9. The delivery system of claim 8 wherein a lead is operably attached to the sensor.

10. The delivery system of claim 8 wherein the sensor is selected from a group consisting of a pressure sensor, a temperature sensor, an oxygen sensor and a flow rate sensor.

11. The delivery system of claim 8 wherein the target site is a body cavity selected from the group consisting of a blood vessel, an aneurismal sac within a blood vessel, and a cardiac chamber, a pleural cavity, a spinal column, an ocular chamber, a cochlea, a subarachnoid space, and a cerebral space.

12. The delivery system of claim 8 wherein the biasing member is comprised of a compressible material such that when the sheath is rotated so that the opening in it is aligned with the sensor, the biasing member expands in a direction lateral to the length of catheter and pushes the sensor through the opening in the sheath.

13. The delivery system of claim 8 wherein the biasing member is comprised of an expandable balloon and a lumen flowably connected to the balloon and to a reservoir of liquid or flowable gel at the proximal end of the catheter, wherein when the system is delivered to the target site, the balloon is filled with the liquid or flowable gel from the reservoir, causing the balloon to expand and push the sensor laterally to the delivery site.

14. A delivery system for delivering a sensor to a target site comprising:
   a catheter;
   a peelable sheath that is perforated along its entire length;
   a sensor within the sheath;
   a lead operably attached to the sensor; and
   a biasing member positioned within the sheath comprising, an expandable balloon, and a lumen flowably connected to the balloon and to a reservoir of liquid or flowable gel at the proximal end of the delivery device, wherein when the delivery device is delivered to a target site, the balloon is filled with the liquid or flowable gel from the reservoir, causing the balloon to expand and press against the perforated peelable sheath, form a break line along the length of the sheath, and push the sensor and the lead through the opening thus formed.

15. The delivery system of claim 14 wherein the sensor is selected from a group consisting of a pressure sensor, a temperature sensor, an oxygen sensor and a flow rate sensor.

16. The delivery system of claim 14 wherein the target site is a body cavity selected from the group consisting of a blood vessel, an aneurismal sac within a blood vessel, and a cardiac chamber, a pleural cavity, a spinal column, an ocular chamber, a cochlea, a subarachnoid space, and a cerebral space.

17. A system for delivering a sensor with a lead attached to the sensor to a target site comprising:
   a catheter, the catheter having a chamber formed therein, proximate a distal end of the catheter;
   a sheath slidably coupled to an exterior surface of the catheter and covering the chamber when in a closed position;
   a wire connected to a proximal end of the sheath;
   a sensor positioned within the interior of the chamber of the catheter and the lead attached to the sensor disposed along the exterior surface of the catheter; wherein, when the system is delivered to a target area within a body cavity, the wire is pushed from a proximal end of the delivery system to cause the sheath to slide toward the distal end of the catheter, thus opening the chamber and releasing the sensor.

18. The system of claim 17 wherein the sensor is selected from a group consisting of a pressure sensor, a temperature sensor, an oxygen sensor and flow rate sensor.

19. The system of claim 17 wherein the target site is a body cavity selected from the group consisting of a blood vessel, an aneurismal sac within a blood vessel, and a cardiac chamber, a pleural cavity, a spinal column, an ocular chamber, a cochlea, a subarachnoid space, and a cerebral space.

20. A method of delivering a sensor to a target site comprising:
   selecting a target site within a body cavity;
   positioning adjacent the target site a catheter having a sheath coupled to the catheter and a sensor within the sheath;
   creating an opening in the sheath to form a clear path of egress between the sensor and the target site; and
   deploying the sensor to the target site, wherein deploying the sensor to the target site further comprises pulling a proximal end of a cord, the cord being operable engaged with a pulley and attached at a distal end to a cap, the cap being engaged with the sensor, wherein, when the cord is pulled, the cap is separated from the sensor.

21. The method of claim 20 wherein the target site within a body cavity is selected from the group consisting of a blood vessel, an aneurismal sac within a blood vessel, and a cardiac chamber.

22. The method of claim 20 wherein the sensor is selected from a group consisting of a pressure sensor, a temperature sensor, an oxygen sensor and a flow rate sensor.

23. The method of claim 20 wherein creating an opening in the sheath further comprises at least partially peeling the sheath.

24. The method of claim 20 wherein creating an opening in the sheath further comprises rotating the sheath so that a delivery opening in the sheath is aligned with the sensor.

25. The method of claim 20 wherein creating an opening in the sheath further comprises causing a break line to form along the length of the sheath.

26. The method of claim 20 wherein creating an opening in the sheath further comprises pushing a wire connected to a proximal end of the sheath and causing the sheath to slide toward the distal end of the catheter.

27. The method of claim 20 wherein deploying the sensor to the target site further comprises allowing a biasing member comprised of a compressible material to move the sensor laterally away from the catheter to the target site.

28. The method of claim 20 wherein deploying the sensor to the target site further comprises filling an expandable balloon with a liquid or flowable gel so the balloon expands and moves the sensor laterally away from the catheter to the target site.

29. A method of delivering a sensor to a target site comprising:
   selecting a target site within a body cavity;
   positioning adjacent the target site a catheter having a sheath coupled to the catheter and a sensor within the sheath;
   creating an opening in the sheath to form a clear path of egress between the sensor and the target site; and
   deploying the sensor to the target site,
   wherein creating an opening in the sheath further comprises rotating the sheath so that a delivery opening in the sheath is aligned with the sensor.

30. The method of claim 29 wherein the target site within a body cavity is selected from the group consisting of a blood vessel, an aneurismal sac within a blood vessel, and a cardiac chamber.

31. The method of claim 29 wherein the sensor is selected from a group consisting of a pressure sensor, a temperature sensor, an oxygen sensor and a flow rate sensor.

32. The method of claim 29 wherein deploying the sensor to the target site further comprises allowing a biasing member comprised of a compressible material to move the sensor laterally away from the catheter to the target site.

33. The method of claim 29 wherein deploying the sensor to the target site further comprises filling an expandable balloon with a liquid or flowable gel so the balloon expands and moves the sensor laterally away from the catheter to the target site.

34. A method of delivering a sensor to a target site comprising:
   selecting a target site within a body cavity;
   positioning adjacent the target site a catheter having a sheath coupled to the catheter and a sensor within the sheath;
   creating an opening in the sheath to form a clear path of egress between the sensor and the target site; and
   deploying the sensor to the target site,
   wherein creating an opening in the sheath further comprises pushing a wire connected to a proximal end of the sheath and causing the sheath to slide toward the distal end of the catheter.

35. The method of claim 34 wherein the target site within a body cavity is selected from the group consisting of a blood vessel, an aneurismal sac within a blood vessel, and a cardiac chamber.

36. The method of claim 34 wherein the sensor is selected from a group consisting of a pressure sensor, a temperature sensor, an oxygen sensor and a flow rate sensor.

37. The method of claim 34 wherein deploying the sensor to the target site further comprises allowing a biasing member comprised of a compressible material to move the sensor laterally away from the catheter to the target site.

38. The method of claim 34 wherein deploying the sensor to the target site further comprises filling an expandable balloon with a liquid or flowable gel so the balloon expands and moves the sensor laterally away from the catheter to the target site.

* * * * *